United States Patent [19]

Merchant et al.

[11] Patent Number: 5,037,661

[45] Date of Patent: Aug. 6, 1991

[54] FUNCTIONAL DECHOLESTEROLIZED EGG YOLKS

[75] Inventors: Zohar M. Merchant, Wilmette; Anilkumar G. Gaonkar, Vernon Hills; R. G. Krishnamurthy, Glenview, all of Ill.

[73] Assignee: Kraft General Foods, Inc., Glenview, Ill.

[21] Appl. No.: 494,764

[22] Filed: Mar. 16, 1990

[51] Int. Cl.⁵ ................................. A23L 1/32
[52] U.S. Cl. .................... 426/47; 426/614; 426/495; 552/545
[58] Field of Search .............. 426/7, 32, 47, 614, 426/495; 260/397.25

[56] References Cited

U.S. PATENT DOCUMENTS

| | | | |
|---|---|---|---|
| 3,260,606 | 7/1966 | Azuma | 426/47 |
| 3,598,613 | 8/1971 | Hawley | 426/47 |
| 4,104,286 | 8/1978 | Fallis et al. | 552/545 |

*Primary Examiner*—Marianne Cintins
*Attorney, Agent, or Firm*—Fitch, Even, Tabin & Flannery

[57] ABSTRACT

The invention herein is a method of reducing cholesterol in egg yolks by extracting cholesterol with substantially low moisture alcohol extractant and then hydrolyzing with selected proteolytic enzymes, such that the resulting product is useful in producing emulsified products like mayonnaise, salad dressings, and the like.

9 Claims, 5 Drawing Sheets

FUNCTIONAL DECHOLESTEROLIZED EGG YOLKS

BACKGROUND OF THE INVENTION

The present invention is directed to highly functional decholesterolized egg yolks and methods for preparing such yolks, as well as emulsified food products such as food dressings utilizing such highly functional decholesterolized egg yolk products.

Egg yolks provide excellent functional emulsification properties for a variety of food products such as food dressings, and are a necessary or desirable component for many food products such as spoonable and pourable food dressings. The functional emulsification properties of egg yolks are believed to be largely attributable to phosphatides, proteins and lipid/protein complex components of the egg yolk. However, in addition to these components which provide functional emulsifying properties, egg yolks also contain triglyceride fats and are also a source of cholesterol, normally containing over one percent by weight of cholesterol. Because it may be desirable, particularly for persons susceptible to coronary heart disease, to limit dietary cholesterol intake to 250-300 milligrams or less per day, it would be desirable to provide functional egg yolk products in which a predominant (i.e., over 85%) amount of the cholesterol has been removed. However, cholesterol, which is present as free cholesterol, and in the form of cholesterol esters of unsaturated and saturated fatty acids, is very difficult to remove from the other egg yolk components, particularly including the triglycerides and functional phosphatide lipoprotein complexes. Nevertheless, substantial effort has been directed to the development of processes for removal of cholesterol from egg yolk. For example, solvent extraction methods employing solvents such as hexane, ethyl ether, and combinations of acetone/hexane, ethanol/hexane, and isopropanol/hexane have been used in an effort to provide decholesterolized egg yolk products. Oil extraction and supercritical carbon dioxide have also been used or proposed. However, such methods have tended to have limited success for a variety of reasons, such as inadequate cholesterol removal, deleterious effects of processing conditions, development of off-flavors, loss of functionality of the extracted egg yolk product, high equipment or processing cost, and/or undesirability of extraction solvent components retained in the finished products.

Improved methods for processing egg yolks to provide highly functional decholesterolized egg yolk products would be desirable, and it is an object of the present invention to provide such methods, and such functional decholesterolized egg yolk products. It is a further object to provide emulsified food products such as salad dressings containing such highly functional egg yolk products, which are substantially cholesterol-free.

These and other objects will be more apparent from the following detailed description and the accompanying drawings.

SUMMARY OF THE INVENTION

The invention herein is a method of decholesterolizing egg yolks, where the resulting product is functionally equivalent to/or better than the starting yolk at significantly lower levels of cholesterol than untreated egg yolks.

The method comprises extracting the cholesterol with an alcoholic solvent followed by hydrolysis with proteolytic enzymes. The alcoholic solvent is substantially low moisture and comprises ethanol, isopropanol or mixtures thereof. After the egg yolks are treated with the alcohol solvent, the egg yolks are enzymatically treated to restore functionality. Alcohol treated egg yolks tend to loose phospholipids, and without the enzymatic treatment the emulsification properties of the product would be poor.

In a particular desirable embodiment the decholesterolized egg yolk product has a free amino nitrogen content of at least over 4000 and preferably in the range of from about 10,000 to about 30,000 micrograms of free amino nitrogen per gram of egg yolk protein. The resulting product has an initial Interfacial Tension of about 9.0 to about 11.0 dynes per centimeter and a final equilibration Interfacial Tension coefficient in the range of from about 3.5 to about 5.5 dynes per centimeter.

The resulting products herein can be useful in producing emulsified products like mayonnaise, salad dressings and the like and are also useful as a flavoring agent in products where egg flavor is needed, or in any other application where a decholesterolized egg yolk is desirable.

DESCRIPTION OF THE INVENTION

Generally, the present invention is directed to methods for providing highly functional decholesterolized egg yolk solids, as well as such products themselves, and substantially cholesterol-free food products such as salad dressings, which utilize the functional properties of such highly functional cholesterol-free food products. By functional egg yolk it is meant an egg yolk product having an interfacial tension comparable to that of control egg yolk which gives a good oil-in-water type emulsion as determined by viscosity/particle size, which is correlatable to texture and viscosity attributes such as pourability. In accordance with the present invention, methods are provided for preparing highly functional, decholesterolized egg yolk products. Generally, such egg yolk products in accordance with the present invention, comprise from about 40 to about 80 weight percent, and preferably from about 60 to about 75 weight percent of egg yolk proteins, from about 10 to about 60 weight percent, and preferably from about 25 to about 40 weight percent of egg yolk lipids (including triglycerides and phopholipids), from about 5 to about 15 weight percent, and preferably from about 5 to about 10 weight percent of egg yolk phosphatides, and less than about 10 weight percent and preferably less than about 3 weight percent moisture, and less than about 0.4 weight percent and preferably less than 0.22 weight percent, of cholesterol, based on the total weight of the egg yolk product. The functional decholesterolized egg yolk product may optionally further comprise up to about 20 weight percent of salt (sodium chloride) as a processing aid and weight percent of the original cholesterol removal therefrom. Other minor amounts of processing aids may also be included. In addition, the decholesterolized egg yolk products of the present invention may include up to about 20 weight percent of vegetable phosphatides, such as food grade soy lecithin (35 weight percent phospholipids). As indicated, the functional decholesterolized egg yolk products of the present invention comprise a relatively high proportion of egg yolk proteins. In particularly desirable embodiments of such decholesterolized egg yolk products, the egg yolk proteins are hydrolyzed by enzyme treatment, particularly at hydrophobic amino acids such as alanine, isoleucine, leucine, phenylalanine and valine to provide a partially protein-hydrolyzed egg yolk having a free amino nitrogen (FAN) content of at least about 4000 and preferably in the a range of from about 10,000 to about 30,000 micrograms of free amino nitrogen per gram of egg yolk protein, dry basis as measured by Church, et al. [Journal of Dairy Science, Vol. 66, pp. 1219-1227 (1983)]. Inhibitors for preferred enzymes include EDTA, and a pH of 4 or less.

Such specific enzyme-hydrolyzed egg yolk protein components may be provided by treatment of egg yolk in aqueous slurry with specific enzymes capable of providing the desired free amino nitrogen content in a limited hydrolysis process. In this regard, the enzymatic proteolysis of extracted egg yolk protein was carried out by addition of the enzyme in an amount sufficient to yield a FAN value in the range of 4000–30,000 and preferably 10,000–30,000 micrograms per gram of egg yolk on a dry basis. Specifically, one part of egg yolk solids was hydrated with 3 parts of water, and 5–10 milligrams of enzyme per gram of hydrated egg yolk was added and the contents shaken for 5 hours at room temperature.

Examples of suitable enzymes are the Rhozyme P41 microbial protease product of Genencor, the Neutrase microbial protease enzyme product of Novo, the Biocon 80,000 microbial protease product of Novo, and the Prozyme 6 microbial protease product of Amano.

Such egg yolk products in accordance with the present invention have a high degree of food emulsion functionality characterized by a relatively low interfacial tension characteristic. Such decholesterolized egg yolk products have an initial interfacial tension coefficient in the range of from about 9.0 to about 11.0 dynes per centimeter, and a final equilibration interfacial tension coefficient in the range of from about 3.5 to about 5.5 dynes per centimeter. By "interfacial tension coefficient" is meant the interfacial tension measured between the water phase and the oil phase in dynes per centimeter at the interface between soybean oil and a 0.2 weight percent dispersion of egg yolk product in one weight percent sodium chloride solution at pH 4.0. By "initial interfacial tension coefficient" is meant the interfacial tension coefficient at a time of 15 seconds from the time of initial contact between the oil and water phase. By "final equilibration interfacial tension coefficient" is meant the interfacial tension coefficient after an equilibration time of 20 minutes.

Such highly functional decholesterolized egg yolk products may be prepared utilizing specific solvent extraction and enzymatic hydrolysis methods in accordance with the present invention. In accordance with such methods, dried egg yolk comprising less than about 5 weight percent water is contacted with a low moisture alcohol extractant comprising ethanol, isopropanol or mixtures thereof. By "low moisture alcohol extractant" is meant an alcohol extractant comprising at least 90 weight percent of ethanol, isopropanol, or mixtures thereof, and less than 10, and more preferably less than 6 weight percent of water. Preferably, the alcohol extractant is substantially anhydrous (i.e., less than 2 weight percent water). The low moisture alcohol extractant is utilized to dissolve a solubilized fraction of the dried egg yolk comprising at least about 20 weight percent of the triglyceride fat content of the dried egg yolk, at least about 85 weight percent of the cholesterol fraction of the dried egg yolk, and less than about 5 weight percent of the protein fraction of the dried egg yolk. Such contacting and dissolution may be carried out at a temperature in the range of from about 10° C. to about 45° C. It may be desirable to carry out the contacting and dissolution steps initially at an elevated temperature in the range of from about 35° C. to about 40° C., to dissolve at least a portion of the triglyceride fats and cholesterol, followed by reduction of the temperature to precipitate triglycerides while substantially retaining the cholesterol in solution.

After a contacting time of at least about 5 seconds, and preferably at least about 2 minutes, the undissolved egg yolk fraction of the extraction suspension is separated from the alcohol extraction solvent and dissolved egg yolk fraction, and the solvent is removed from the solid phase extracted fraction. Treatment of egg yolks with the low moisture alcohol extractant leads to removal of components other than fat and cholesterol, particularly including phospholipids. The phospholipids are present in egg yolks as lipoprotein complexes which provide emulsification functionality. Removal of these phospholipids may lead to aggregation of the egg yolk proteins and lowering of egg yolk functionality. To restore functionality, the decholesterolized egg yolks may be reconstituted with vegetable phosphatides such as food grade soybean lecithin, or the original food grade phosphatides may be recovered and returned to the egg yolk solids, as will be described in more detail. Alternatively, specific enzymatic hydrolysis of the decholesterolized egg yolks may be carried out to increase its functionality. It is an important aspect of the present disclosure that the extracted solid phase fraction may be enzymatically hydrolyzed under specific conditions to provide a desired free amino nitrogen content, and decrease the interfacial tension coefficient.

Figure 1:
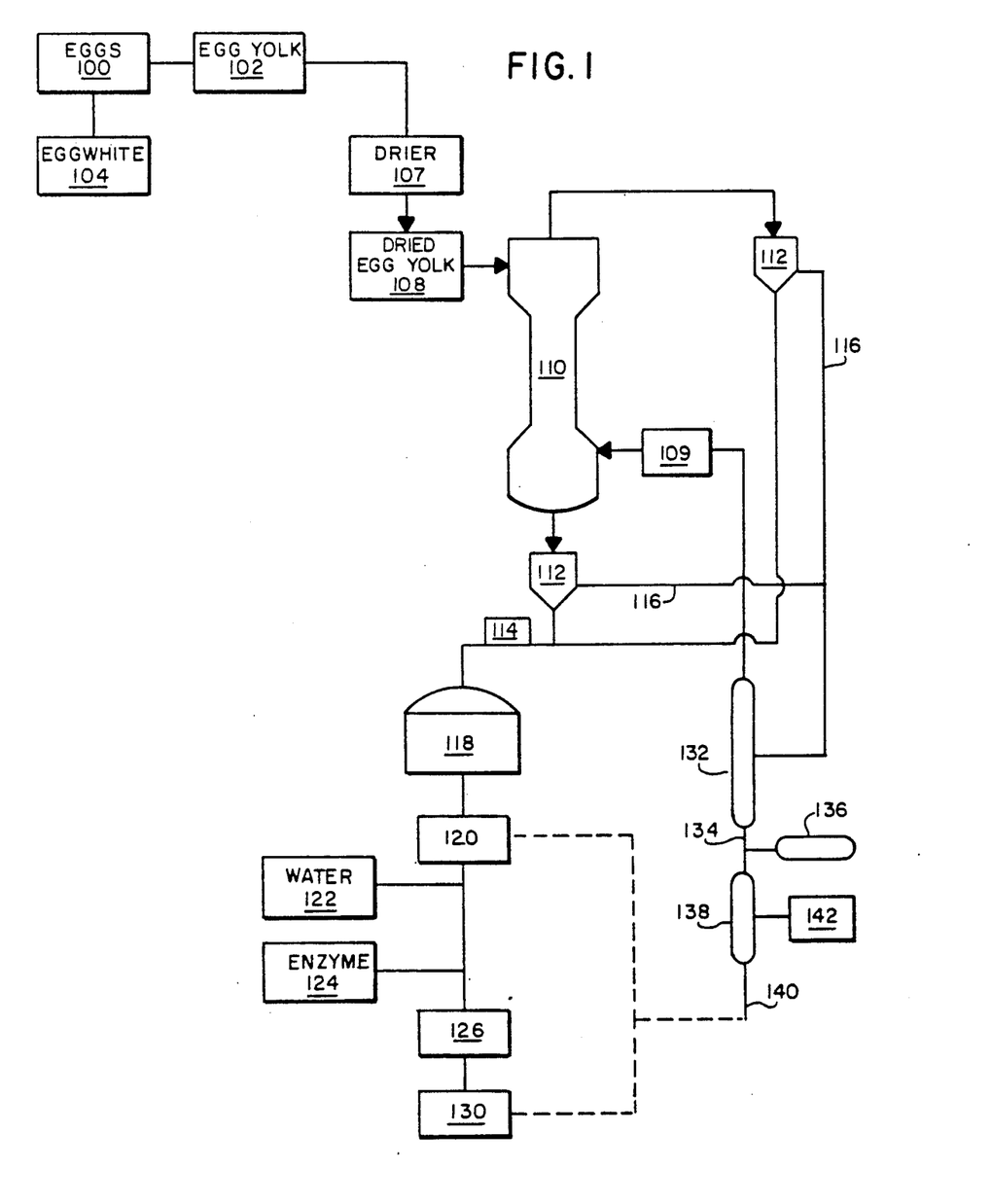
FIG. 1 is a schematic block diagram of an embodiment of a method in accordance with the present invention for providing decholesterolized, highly functional egg yolk products.

Methods for preparation of decholesterolized, highly functional egg yolk products will now be more particularly described with respect to the process flow diagram of FIG. 1. As shown in FIG. 1, dried poultry egg yolks, preferably chicken egg yolks, are provided having a moisture content which is less than about 10 weight percent and preferably in the range of from about 2 to about 4 weight percent, based on the weight of the dried egg yolk product.

The liquid yolks 102 of fresh whole chicken eggs 100 are typically separated from the liquid egg white components 104 by mechanical breakers and separators in accordance with conventional practice. The liquid yolk product 102, which is typically at least about 90 weight percent of yolk and less than 10 weight percent of liquid egg white, will usually contain at least about 0.5 weight percent of cholesterol, a maximum of about 57 weight percent of water, at least about 25 weight percent of fat, and from about 15 to about 17 and typically about 16 weight percent of protein, as well as from about 8 to about 11 weight percent of phospholipids. Egg yolk phospholipids such as phosphatidyl choline and phosphatidyl-ethanolamine are generally complexed with egg yolk protein. Such complexes are believed to be providing superior functional emulsion characteristics. Up to about 10 weight percent salt (sodium chloride) based on the total product weight may be added to the liquid egg yolk prior to drying as a preservation agent. Other components such as anti-caking agents may also be added to the yolk prior to drying in accordance with conventional practice. The liquid egg yolks 102 may, if desired, be pasteurized prior to drying, such as by heating the yolk to a temperature of about 140° F. for about 3.5 minutes, or equivalent time-temperature conditions. However, in order to preserve the functionality of the egg yolk product, the yolk should best not be heated above a temperature of about 45° C. The egg yolk 102 may be dried directly in a dryer such as a spray dryer 107 to provide dried egg yolk 108, or may first be stabilized by removal of free glucose, such as by use of a glucose-oxidase enzyme in accordance with conventional methods for dried egg yolk preparation.

The egg yolk is dried in any suitable manner such as by spray drying, drum drying or freeze drying in dryer 107, to provide a moisture level of from about 2 to about 4 weight percent in the dried egg yolk product 108. The drying process, however, should not substantially adversely affect the functionality of the egg yolk. The dried egg yolk 108 comprises at least about 96 weight percent total solids, at least about 1.8 weight percent of cholesterol, at least about 57 weight percent egg yolk fat, and from about 30 to about 37 weight percent of egg yolk protein, typically, about 33 weight percent protein. As shown in FIG. 1, the dried egg yolk 108 is mixed with a substantially water-free alcohol extractant 109 comprising ethanol, isopropanol, or mixtures thereof, in a dried egg yolk to alcohol extractant solution weight ratio in the range of from about 1:1 to about 1:10, and preferably in the range of from about 1:3 to about 1:8 at a temperature in the range of from about 20° to about 35° C. It is important that the alcohol extractant have very low moisture content, and that the dried egg yolk have minimal water content as previously described, to achieve a suitable extraction in accordance with the present methods. If the extraction mixture contains more than about 10 weight percent of water, significant amounts of protein are lost. The extraction may be carried out by batch extraction techniques, or by continuous co-current, or countercurrent solid-liquid extraction techniques. In the illustrated embodiment, the extraction may be carried out in a batch or continuous countercurrent solid-liquid extractor 110.

The egg yolk solids, which primarily comprise egg yolk proteins including highly functional phospholipid/protein complexes, are separated from the solution phase of the extraction mixture which primarily contains the egg yolk fat components and an enriched cholesterol component. The insoluble solid egg yolk phase of the alcoholic extraction suspension in the countercurrent contactor 110 which includes solids which have passed through the contactor in a countercurrent manner, and any very fine suspended solid material which may have been swept away by the solvent, is separated by separators 112 to provide a separate solid phase 114 and an extraction solution phase 116. The solid phase yolk product 114 which is separated from the alcohol extraction mixture should comprise less than 0.4 weight percent of cholesterol, and preferably less than 0.2 weight percent of cholesterol, based on the total solids content of the extracted egg yolk solids component, and should comprise at least about 60 weight percent of the initial dried egg yolk protein component. The solubilized cholesterol-containing extraction mixture 116 should comprise at least about 85 weight percent of the cholesterol, and preferably at least about 90 weight percent of cholesterol, and less than about 5 weight percent of the protein of the dried egg yolk 108.

The egg yolk solid phase components of the extraction mixture may be separated in any appropriate manner from the extraction solution, such as by filtration or centrifugation. The separated solids 114, particularly if batch extraction methods are employed, may be washed with a small amount of fresh, substantially water free alcoholic extraction solvent.

The separated, alcohol extracted yolk solids are subsequently dried to remove residual solvent, to a level of less than about 1000 ppm by weight, based on the total weight of the extracted yolk solids to provide a cholesterol depleted egg yolk product 120. The extracted egg yolk may be provided with food grade antioxidants such as tocopherols, tertiary butyl hydroquinone, in effective amounts, prior to the drying step. In this regard, the yolk solids may be subjected to a vacuum treatment in a vacuum dryer 118 at a vacuum of less than 20 millimeters and preferably less than 10 millimeters of mercury for a length of time sufficient to achieve substantially complete solvent removal.

The use of a substantially water-free alcohol extractant such as an isopropanol and/or ethyl alcohol extractants at moderate temperatures, and removal of solvent under reduced pressure, has limited deleterious effect on the egg yolk. However, the alcohol extracted decholesterolized egg yolk solids 120 have reduced functionality in comparison with the dried egg yolk 108.

Treatment of egg yolks with the low moisture alcohol extractant leads to removal of components other than fat and cholesterol, particularly including phospholipids. The phospholipids are present in egg yolks as lipoprotein complexes which provide emulsification functionality. Removal of these phospholipids may lead to aggregation of the egg yolk proteins and lowering of egg yolk functionality. To restore functionality, the decholesterolized egg yolks may be reconstituted with vegetable phosphatides such as soybean lecithin, or the original phosphatides may be recovered and returned to the egg yolk solids, as will be described in more detail. Alternatively, specific enzymatic hydrolysis of the decholesterolized egg yolks may be carried out to decrease the aggregation and thereby increase the functionality of the decholesterolized egg yolk. In this latter regard, the cholesterol-depleted egg yolk solids 120 are subjected to enzymatic hydrolysis in hydrolysis reactor 126 to restore or increase the functionality of the egg yolk product. In this regard, the dried cholesterol-depleted egg yolk solids 120 are mixed with water 122 and an enzyme 124 capable of providing a free amino nitrogen group content (FAN) of at least about 4,000, and preferably in the range of from about 10,000 to about 30,000 micrograms per gram of egg yolk protein on a dry basis.

In the illustrated embodiment, the cholesterol-depleted egg yolk solids are slurried with water in a ratio of from about 1:2 to about 1:5 on a weight to weight ratio basis and 0.5 weight percent of the Neutrase microbial enzyme product of Novo, based on the weight of the cholesterol depleted egg yolk solids, for 5 hours in a hydrolysis reactor 126 at ambient temperature to provide a decholesterolized hydrolyzed egg yolk 130. Without limiting the scope of the invention, it is theorized that this improved functionality may be due to the disaggregation of egg yolk protein components which were agglomerated by the alcohol extraction step, and/or the formation of lower molecular weight amphiphillic peptides which may migrate to the interface in an oil-water emulsion of the emulsified food product. The hydrolysis of the decholesterolized egg yolk 120 restores its functionality to provide a superior decholesterolized product 130.

As also indicated, the native phospholipids which are dissolved by the low moisture alcohol extractant may be returned to the cholesterol-depleted egg yolk 120 or 130. In this regard, as shown in FIG. 1, the alcohol extractant supernatant 116 comprises primarily dissolved triglycerides, cholesterol and phospholipids. The alcohol extraction solvent may be removed from the supernatant 116 by evaporator 132 to provide extraction solvent 109 recycle use, and an egg yolk oil 134. The cholesterol component of the egg yolk oil 134 may be selectively removed by use of suitable selective adsorbent such as activated carbon, Florisil, cyclodextrins, Vitamin D or silicic acid in a tank or column 138. A suitable solvent 136 to enhance the selective adsorption may be used if desired. The cholesterol removal step should best remove at least 70 percent of the cholesterol from the oil 134, to provide a cholesterol-depleted extract 140 comprising triglycerides and phospholipids, and a cholesterol stream 142. The cholesterol-depleted oil extract 140 should comprise at least about 75 weight percent phospholipids, and less than about 15 weight percent cholesterol. The cholesterol-depleted extract 140 may optionally be recombined with the cholesterol-depleted egg yolk 120 or with hydrolyzed egg yolk 130 by blending these components in alcohol, followed by alcohol removal.

The egg yolk products produced in accordance with the present invention may be utilized to prepare substantially cholesterol-free emulsified food products such as viscous and pourable dressings, in the same manner as the preparation of such products using conventional egg yolks. However, because of the high degree of functionality of the decholesterolized egg yolk products produced in accordance with the present invention, smaller amounts of the decholesterolized yolk product may be utilized to produce the same functional effect of a large weight percentage of conventional egg yolk.

Having generally described the present invention, various aspects of the invention will now be described with respect to the following specific examples.

EXAMPLE 1

Dried egg yolks (400 g) having less than 5 weight percent moisture were extracted with 1300 milliliters (1:3.3 w/v ratio) of anhydrous ethanol or anhydrous isopropanol. The mixtures were stirred for 10 minutes and centrifuged. The residual solvent from the centrifuged egg yolk solid was removed under vacuum at 25°–35° C. The yield and analysis data are given in Table 1.

TABLE 1

| Analysis of Solvent Extracted Egg Yolks | | | |
|---|---|---|---|
| | Control* | Isopropanol | Ethanol |
| Egg Yolk/Solvent | — | 1:3.3 | 1:3.3 |
| Yield (grams) | . | 220 | 300 |
| Yield % | — | 55 | 75 |
| Amt of Cholesterol in egg yolks (grams) | 8.0 | 2.2 | 3.3 |
| % Removal of Cholesterol | — | 72 | 59 |
| % Removal of Proteins | — | 3.0 | 7.5 |
| Amt Phospholipids in egg yolks (grams) | 69.4 | 44.0 | 31.1 |

TABLE 1-continued

| Analysis of Solvent Extracted Egg Yolks | | | |
|---|---|---|---|
| | Control* | Isopropanol | Ethanol |
| % Removal of Phospholipid | — | 37 | 45 |

*Weight of the starting dried egg yolk was 400 grams in each experiment

Protein analysis was performed by measuring nitrogen according to the AOAC procedure (AOAC, Kjeldahl Method, 70.26 & 7.032, 14th Edition, 1984) and multiplying by a factor of 6.25. Cholesterol analysis was performed measuring the total cholesterol (including cholesterol esters) as cholesterol by gas chromatography [Tsui, I., Assoc. Off. Anal. Chem., 72(3), 421 (1989)]. The phospholipids were analyzed by high pressure liquid chromatography (HPLC) using known standards for egg yolk phospholipids. The extracted egg yolks solids have 59% and 72% cholesterol reduction and a 45% and 37% reduction in phospholipids with ethanol and isopropanol, respectively.

EXAMPLE 2

The dried egg yolks (400 grams) having less than 5 weight percent moisture were extracted with anhydrous ethanol and anhydrous isopropanol in a similar fashion as in Example 1, except that the extraction and centrifugation procedures were repeated 2 additional times using 1370 ml and 1330 ml of solvent for 400 grams egg yolk powder. The residual solvent from the final centrifuged egg yolk solid was removed under reduced pressure at 25°–35° C. The yield and analysis data are given in the following table:

TABLE 2

| Analysis of Solvent Extracted Egg Yolks | | | |
|---|---|---|---|
| | Control* | Isopropanol | Ethanol |
| Egg Yolk/Solvent | — | 1:10 | 1:10 |
| Yield (grams) | — | 200 | 220 |
| Yield % | — | 50 | 55 |
| Amt of Cholesterol in egg yolks (grams) | 8.0 | 0.4 | 0.7 |
| % Removal of Cholesterol | — | 95 | 92 |
| % Removal of Proteins | — | 7.5 | 4.5 |
| Amt Phospholipids in egg yolks (grams) | 69.4 | 27.2 | 49.0 |
| % Removal of Phospholipid | — | 61 | 70 |

*Weight of the starting dried egg yolk was 400 grams in each experiment

There was retention of flavor and no substantial loss of protein. The protein gel profile of the extracted egg yolk was similar to that of the control. There was loss of somewhat more lipids, including phospholipids, than in the experiments of Example 1, but also removal of more cholesterol. The extracted egg yolk solids had 92% and 95% cholesterol reduction, and negligible protein loss of 5% and 7% with ethanol and isopropanol extraction at a 1:10 w/v ratio, respectively.

EXAMPLE 3

The solvent extracts from ethanol or isopropanol runs in Example 2 were mixed with activated charcoal at a ratio of 100 milligrams or 500 milligrams per 2-2.5 milliliter of the solvent extract. The mixture was vortexed for 30 seconds, shaken for another 10 minutes, and filtered or centrifuged to separate the charcoal. Such charcoal treatment resulted in removal of 60–70% of the cholesterol, and only about 30% of the phospholipids. There was no significant cholesterol removal with cholestyramine. Other techniques for separation of cholesterol from the extracted egg yolk component, such as silica gel column fractionation may also be used to remove cholesterol from the extracted phospholipids and other lipid components. Such charcoal treatment may be used to preferentially remove cholesterol from the egg yolk lipids and phospholipids which are removed with cholesterol in the ethanol or isopropanol extractant. The egg yolk phospholipids are very important in providing the functional properties of egg yolk such as its emulsification capacity. The decholesterolized egg yolk lipids, and particularly the egg yolk phospholipids thereof, may be recombined with the decholesterolized egg yolk product from which they were earlier extracted, to provide a highly functional egg yolk product.

EXAMPLE 4

In addition to recombination with decholesterolized extractant components of the egg yolk, functionality of the extracted egg yolks may be restored or increased by supplementation with other phospholipids. Towards this end, the type of egg yolk phospholipids extracted were determined as follows: Control unextracted dried egg yolk (5 g) were extracted with chloroform/methanol (2:1 v/v, 33.3 ml × 3) to achieve complete delipidation. The rest of the procedure was similar to that described by Folch, et al. [J. Biol. Chem., 226, 497 (1957)]. Yield was 2.8 grams. The extracted lipids were analyzed for phospholipids by high performance liquid chromatography (HPLC) using phospholipid standards and P-31 nuclear magnetic resonance spectroscopy [Sotirhos, et al., J. Lipid Res. 27, 386 (1986)]. The HPLC data gave the absolute proportions of phospholipids and nmr the relative proportions. This data established that the major phospholipids present in the unextracted egg yolks to be phosphatidycholine (PC) and the phosphatidylethanolamine (PE) in the ratio of 80:20, as shown in the following table:

TABLE 3

| Proportion of Major Phospholipids Extracted from Egg Yolk by Solvent Treatment | | | | |
|---|---|---|---|---|
| | Proportion of PC-PE | | | |
| | HPLC | | P-31 NMR | |
| Sample | PC | PE | PC | PE |
| Control (2:1 CHCl$_3$:MeOH) | 80.8 | 19.2 | 80.1 | 19.9 |
| 1:3 Ethanol | 79.1 | 20.9 | 81.5 | 18.5 |
| 1:10 Ethanol | 82.2 | 17.8 | 79.5 | 20.5 |
| 1:3 Isopropanol | 79.9 | 20.1 | 82.0 | 18.0 |
| 1:10 Isopropanol | 80.3 | 19.7 | 80.5 | 19.5 |

The major phospholipids in the egg yolks (Examples 1 and 2) extracted by ethanol or isopropanol showed no substantial difference in the proportion of phosphatidylcholine (PC) and phosphatidylethanolamine (PE) removed as compared to that present in the control unextracted egg yolks (Table 3). Commercially available egg lecithin or soybean lecithin having comparable proportions of PC:PE may accordingly be added to the alcohol-extracted egg yolks to increase the functionality of the decholesterolized egg yolk product.

EXAMPLE 5

Figure 2:
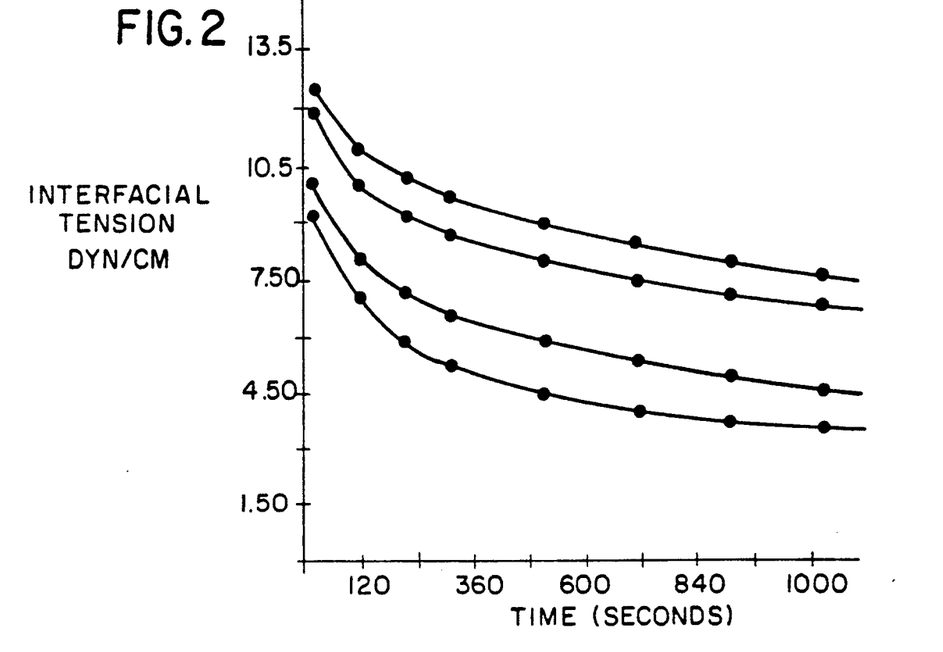
FIG. 2 is a graph of the interfacial tension in a water-soybean oil system of a standard cholesterol-containing egg yolk as compared to various decholesterolized egg yolk products, as a function of time.

The functionality of egg yolk products in food emulsion systems may be correlated with and quantified by the interfacial tension (IT) between the respective egg yolk solutions and the oil component of the emulsion. The IT was determined using the Wilhelmy plate method as generally described in the literature [Gaonkar, A. G., J. Oil Chemists Soc. 66 (8), 1090 (1989)]. The results of such IT measurements for 0.2% solutions of respective egg yolks (control dried egg yolk and ethanol or isopropanol-extracted egg yolk solids in the presence of 1 weight percent NaCl in the aqueous phase, at pH 4.0 against soybean oil (commercial sample) are shown in FIG. 2, as interfacial tension curves 202, 204, respectively. It should be emphasized that the values of the IT are strongly dependent on the pH, concentration of the egg yolk and salt (NaCl) and purity of the oil. Therefore, comparisons should be made relative to the control egg yolk.

It is evident from FIG. 2 that the extracted egg yolk (curve 204) exhibited an increase in the IT compared to the control egg yolk (curve 202), thereby indicating that the extracted egg yolk is substantially less surface active than the control egg yolk.

EXAMPLE 6

Extraction with solvent removes functional phospholipids (PL's), which may lead to aggregation of egg yolk proteins and reduction in its emulsification properties. In accordance with one aspect of the present disclosure, the lipoprotein complexes may be reformed by addition of lecithin to the extracted egg yolks to increase their functionality. In this regard, a number of runs were carried out in which extracted egg yolk solids (250 mg) were hydrated with water (750 microliters) and left standing at 4° C. for 1 hour and soybean lecithin (25 to 250 mg, actual PL content was 8 to 80 mg) was added under stirring. The mixtures were held overnight at 4° C. and used directly or after freeze drying for interfacial tension studies. It was observed that 3 to 10 weight percent of added phospholipid, relative to the weight of the dried extracted egg yolk solids, provided substantially equivalent interfacial tension values to that of the unextracted control egg yolk. However, if salt was present at 1% in the egg yolk-lecithin mixture, the interfacial tension profiles were similar to that of free lecithin. This suggested that the lipoprotein complex was unstable in presence of salt. This instability was further supported by differential scanning calorimetry (DSC) measurements.

EXAMPLE 7

Mayonnaise products were made from the control egg yolks and extracted egg yolk solids obtained from Example 2 using the following component formula:

| Ingredients | A | B |
| --- | --- | --- |
| Soybean oil | 78.4% | 77.8% |
| Water | 13.6% | 15.5% |
| Sugar/Salt/Spice/Flavorings | 2.6% | 2.6% |
| Vinegar | 2.4% | 2.4% |
| Control egg yolk | 2.5% | — |
| Extracted egg yolk solids | — | 1.2% |
| Dried egg white | 0.5% | 0.5% |

The control mayonnaise product was prepared using the formulation A as follows: First, the egg yolk was hydrated in a mixing bowl to which was added sugar, salt, spices, flavoring agents and the part of the water. The oil was slowly added (with stirring and the speed setting of the Hobart mixer set at 3) in small increments. When half of the oil was added, the speed was reduced to medium speed (speed setting knob at 2) and the remaining oil was added, followed by incremental addition of remaining water and vinegar to form a pre-mix. The pre-mix was homogenized in a Gaulin colloid mill (flow setting at 15 and gap setting at 10). Rheological yield value, viscosity, centrifugal stability, particle size, protein content and cholesterol in mayonnaise sample were determined.

Initial rheological yield value and viscosity were obtained using a Haake VT 24 viscometer with a 4-blade spindle (blade dimensions = $19 \times 17 \times 1$ mm$^3$; rod length = 210 mm; rod diameter = 5 mm). The yield is the initial maximum value reached. The viscosity is the Haake value at 1 minute. For determining the centrifugal stability, 63 to 64 grams of the mayonnaise sample was spun in a centrifuge tube at 10,000 rpm ($4000 \times g$) for 20 minutes and the amounts of separated serum and oil were measured. The particle size of the emulsion was also measured using a Leeds & Northrup Microtrac analyzer.

A second mayonnaise product was prepared in the same manner as the first mayonnaise but employing the ethanol and isopropanol extracted egg yolk solids (described in Example 2), according to Formula B. The level of the extracted egg yolk solids needed to provide the emulsion was less than half of that required for the control mayonnaise.

Emulsion characteristics of mayonnaises prepared using Formula A and B are given in the following Table 4:

TABLE 4

Characteristics of Mayonnaises Prepared Using Control and Alcohol Extracted Dried Egg Yolks

| Yolk | % Chol. Relative to Control | pH | Oil Drop Size (μ) | Yield/ Viscosity (Haake units) |
| --- | --- | --- | --- | --- |
| Control dried egg yolk | 100% | 3.8 | 4.1 | 2700/1050 |
| Ethanol Ext. Egg yolk solids (Example 2) | <10%* | 3.9 | 16.2 | >3200/2600 |
| Isopropanol Ext. Egg yolk solids (Example 2) | <10%* | 3.8 | 12.6 | >3200/2700 |

*Resulting in cholesterol values of <2 mg per serving

The centrifugal stability of each of the mayonnaise products of Table 4 was such that less than 0.2 grams of oil separated under the centrifugation test conditions.

EXAMPLE 8

Enzymatic hydrolysis was performed on extracted egg yolk solids to improve its functionality. Extracted egg yolks from Example 2 were hydrated with water at the w/w ratio yolk solids to water of 1:3 and were hydrolyzed with 0.5 weight percent of a variety of enzymes at room temperature. Hydrolysis was continued for 5 hours and was then terminated to prevent microbial spoilage. The incubation time can be reduced significantly by increasing the amount and/or purity of enzymes, and/or the incubation temperature. The hydrolyzed, extracted egg yolks were analyzed for free amino nitrogen (FAN) according to the procedure of Church, et al. [J. Dairy Sci., 66, 1219 (1983) and Joys, et al., Anal. Biochem., 94, 371 (1979)] for measuring primary amino groups released by proteolysis. Interfacial tension measurements were performed using the hydrolyzed decholesterolized egg yolk as described in Example 5. Mayonnaises were also prepared using the hydrolyzed extracted egg yolk. The specific enzymes used and the FAN values of the enzyme-treated, decholesterolized egg yolk product, in micrograms of free amino nitrogen per gram of egg yolk protein (dry basis) are shown in Table 5.

TABLE 5

Free Amino Nitrogen (FAN, μg/g of egg protein) for Isopropanol-Extracted Egg Yolk Solids Hydrolyzed with Different Enzymes

| Enzyme | FAN (μg/g Egg protein) |
| --- | --- |
| Untreated | 3290 |
| Prozyme 6 (Amano) (PR6) | 23226 |
| Neutrase (Novo) (N) | 12903 |
| Rhozyme P41 (Genencor) (RP41) | 12903 |
| Biocon 80,000 (Novo) (B80) | 5742 |
| Pancreatic Trypsin (Novo) (PT) | 2903 |
| Palatase (Novo) (PLT) | 3613 |
| Pure Porcine Trypsin (Novo) (PPN) | 3677 |
| Rennilase (Novo) (RN) | 3871 |

The data from Table 4 indicate that FAN values in the case of extracted egg yolk solids (untreated), PT, PLT, PPN, RN and B80 were low, while with N, RP41 and PR6 were high.

The interfacial tension of the control egg yolk, extracted egg yolk solids and enzyme hydrolyzed extracted egg yolks was determined as described in Example 5. The treatment of extracted egg yolk solids with enzymes listed in Table 4 resulted in lowering of IT to different degrees. This is illustrated in FIG. 2 by the interfacial tension curves for the hydrolysis products of Neutrase and Trypsin treatment of decholesterolized egg yolk, respectively. The interfacial tension curve 206 Neutrase treated, decholesterolized egg yolk is a preferred embodiment which is closer to the control egg yolk curve 202. The least desirable performance was that provided by the Trypsin-treated decholesterolized egg yolk product, as shown by curve 208, which is closer to the extracted egg yolk solids curve 204.

Mayonnaise emulsions were prepared using the hydrolyzed extracted egg yolks employing essentially the same formula and procedure as described in Example 7. The emulsion characteristics of mayonnaises thus prepared are shown in Table 6.

TABLE 6

Characteristics of Mayonnaise Prepared Using Cholesterol-Depleted Egg Yolks and Enzyme-Hydrolyzed Cholesterol-Depleted Egg Yolks

| Enzyme | Haake Yield | Haake Viscosity | Texture |
| --- | --- | --- | --- |
| Untreated | >3200 | 2080 | Bad |
| Rhozyme P41 (Genencor) | 1900 | 700 | Good |
| Neutrase (Novo) | 2300 | 1100 | Good |
| Biocon 80,000 (Novo) | 1900 | 680 | Good |
| Prozyme 6 (Amano) | 2100 | 820 | Good |
| Pancreatic Trypsin (Novo) | >3200 | 1520 | Bad |
| Pure Trypsin (Novo) | 2900 | 1500 | Bad |
| Rennilase (Novo) | >3200 | 1840 | Bad |
| Palatase (Novo) | >3200 | 2120 | Bad |

The data showed that the functionality of the extracted egg yolk solids is considerably improved when the FAN value is at least 4000 micrograms per gram of egg yolk protein (on a dry basis), an IT value approaching that of the control egg yolk and this agrees with the mayonnaise results shown in Table 4.

Figure 3:
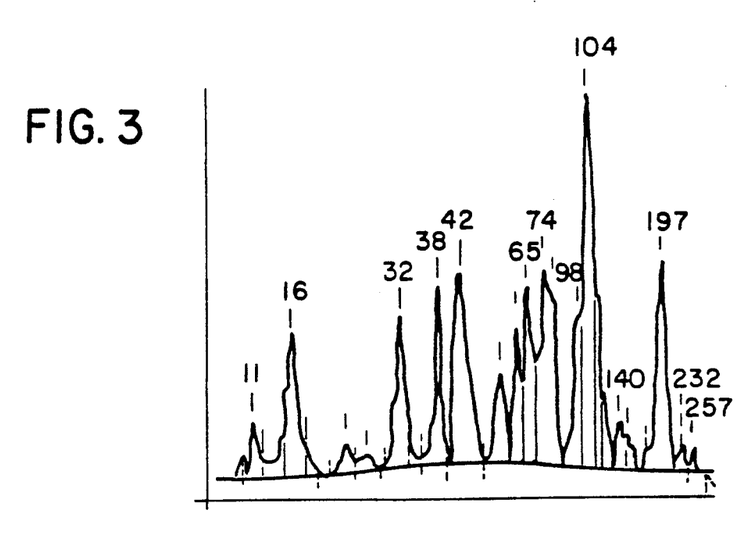
FIG. 3 is a graphic representation of the proportions of protein components by polyacrylamide gel electrophoresis (PAGE), as a function of molecular weight in Daltons, of a decholesterolized dried egg yolk starting material for the method of FIG. 1.
Figure 4:
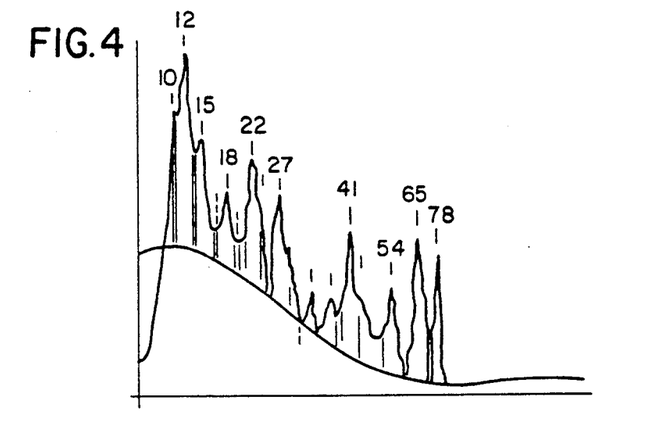
FIG. 4 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with a specific microbial hydrolase (Prozyme 6-Amano)
Figure 5:
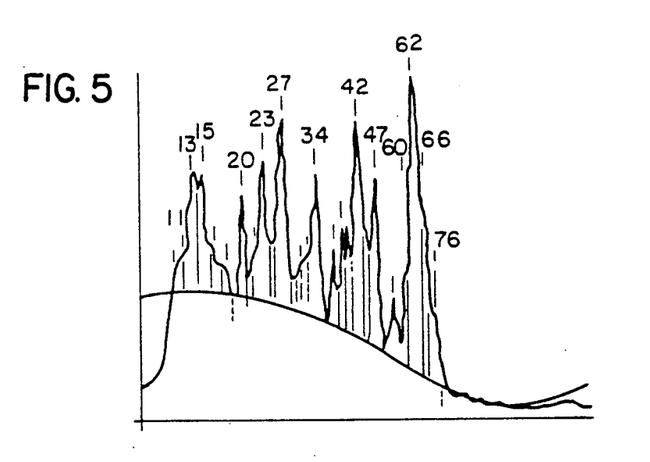
FIG. 5 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with a specific microbial hydrolase (Neutrase-Novo)
Figure 6:
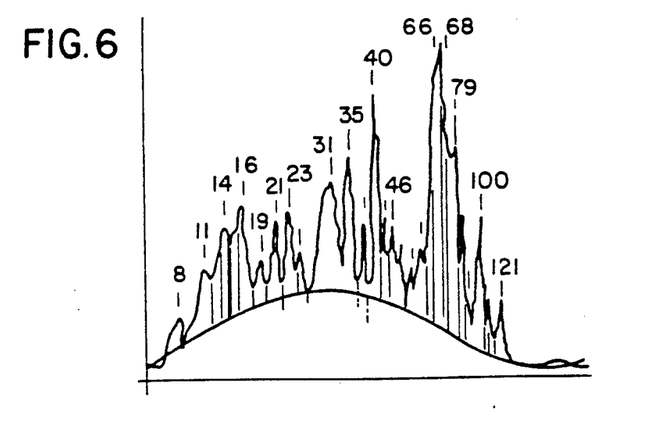
FIG. 6 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with a specific microbial hydrolase (Rhozyme P41-Genencor)
Figure 7:
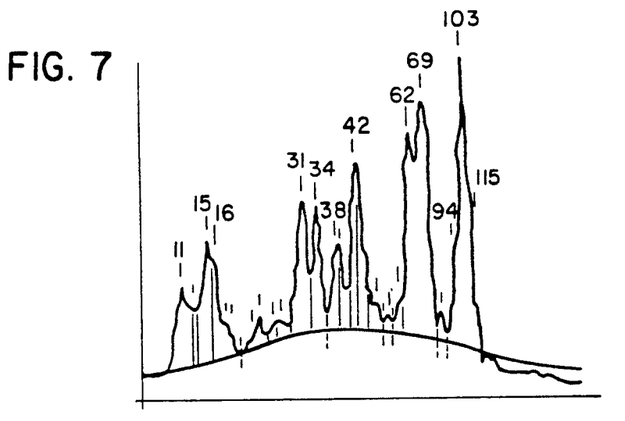
FIG. 7 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with a specific microbial hydrolase (Biocon 80,000-Novo)
Figure 8:
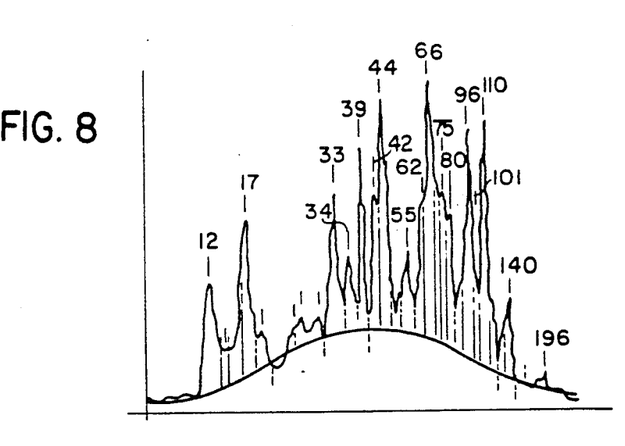
FIG. 8 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with pancreatic trypsin.
Figure 9:
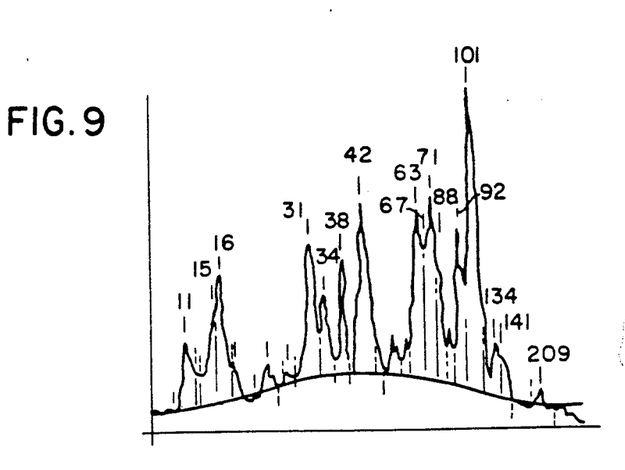
FIG. 9 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with a specific fungal hydrolase (Palatase-Novo)
Figure 10:
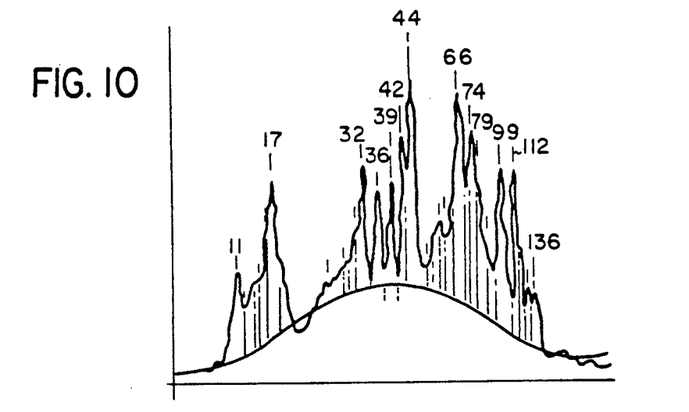
FIG. 10 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with pure porcine trypsin.
Figure 11:
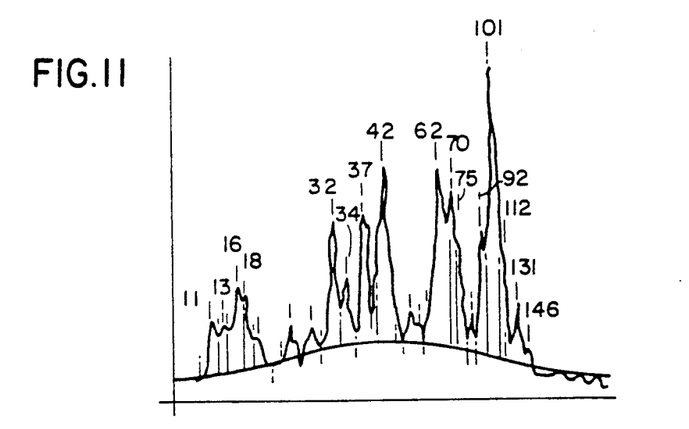
FIG. 11 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with a specific microbial hydrolase (Rennilase-Novo)
Figure 12:
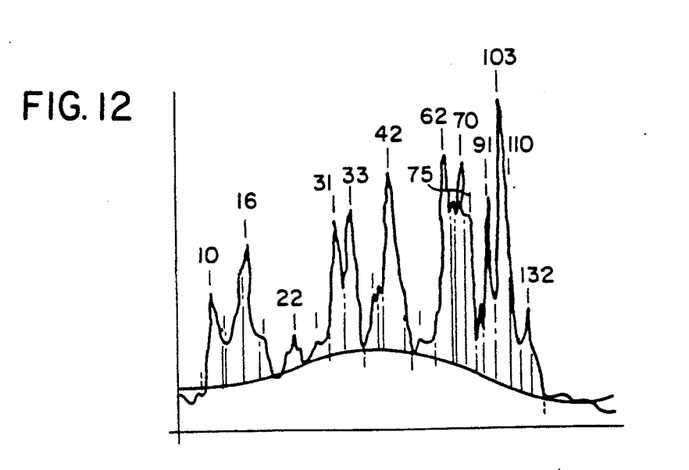
FIG. 12 is a graphic representation of the proportions of protein components by polyacrylamide gel electrophoresis (PAGE), as a function of molecular weight in Daltons, of a decholesterolized egg yolk like that of FIG. 3 which has been enzymatically hydrolyzed with lipase (AP6-Amano).

The hydrolyzed, enzyme-treated decholesterolized egg yolk products were also analyzed by polyacrylamide gel electrophoresis to provide a molecular weight profile. A lipase enzyme (Lipase AP6-Amano) is also used to treat decholesterolized egg yolk in substantially the same manner as the other enzymes. The results of such PAGE analyses are shown in FIGS. 3-11, with major peaks identified by their respective molecular weights, in kilodaltons, as follows:
FIG. 3 Decholesterolized dried egg yolk
FIG. 4 (Prozyme 6-Amano)
FIG. 5 (Neutrase-Novo)
FIG. 6 (Rhozyme P41-Genencor)
FIG. 7 (Biocon 80,000-Novo)
FIG. 8 pancreatic trypsin
FIG. 9 (Palatase-Novo)
FIG. 10 pure porcine trypsin
FIG. 11 (Rennilase-Novo)
FIG. 12 Lipase (AP6-Amano)

It is noted that the enzyme-treated products which provided good texture in the mayonnaise formation tend to have an increased amount of components in the molecular weight range of from about 16,000 to about 31,000, and decreased amounts of components at molecular weights above 125,000 and preferably decreased amounts of components above 80,000 molecular weight.

The results illustrate successful development of cholesterol-free mayonnaise using hydrolyzed extracted egg yolk solids comparable in texture and viscosity to that prepared using control unextracted egg yolks.

Accordingly, it will be appreciated that in accordance with the present invention, functional decholesterolized egg yolk product have been provided, as well as methods for providing such egg yolk product, which may be used to provide high quality, substantially cholesterol-free emulsified food product. While the invention has been specifically described with respect to various specific embodiments, it will be appreciated that various modifications and adaptations will be apparent from the present disclosure, which are intended to be within the scope of the following claims.

What is claimed is:

1. A method for providing a functional decholesterolized egg yolk product comprising the steps of
   providing dried egg yolk having a moisture content of less than about 5 weight percent, contacting the dried egg yolk with a substantially low moisture alcohol extractant comprising ethanol, isopropanol, or mixtures thereof to form an extraction mixture, separating a solid phase egg yolk component from the liquid phase of the extraction mixture and removing substantially all of the extraction mixture and removing from the extracted egg yolk solid substantially all of the solvent, to provide a cholesterol-depleted egg yolk product, and hydrolyzing the cholesterol-depleted egg product with a proteolytic enzyme to provide a cholesterol-depleted, hydrolyzed egg yolk product having an interfacial tension coefficient substantially the same as that of unextracted dried egg yolk.

2. A method in accordance with claim 1 wherein said hydrolyzed egg yolk product has a FAN of at least about 4000 micrograms per gram of egg protein, on a dry basis.

3. A method in accordance with claim 2 wherein said hydrolyzed egg yolk product has a FAN in the range of from about 10,000 to about 30,000 micrograms per gram of egg protein, on a dry basis.

4. A method in accordance with claim 1 wherein said hydrolyzed egg yolk product has an initial interfacial tension coefficient in the range of from about 9 to about 11 dynes/cm, and a final interfacial tension coefficient in the range of from about 3.5 to about 5.5 dynes/cm, which is comparable to the range for unextracted control dried egg yolk when measured under the conditions employing 0.2 percent egg yolks in the presence of 1 weight percent sodium chloride in the aqueous phase, at pH 4.0 against soybean oil.

5. A hydrolyzed decholesterolized egg yolk product having a FAN in the range of from about 10,000 to about 30,000 micrograms per gram of egg protein, on a dry basis.

6. An oil-in-water type food emulsion comprising water, vegetable oil and a hydrolyzed decholesterolized egg yolk product, said hydrolyzed decholesterolized egg yolk product having a in the range of from about 10,000 to about 30,000 micrograms per gram of egg protein, on a dry basis FAN and a final interfacial tension coefficient in the range of from about 3.5 to about 5.5 dynes/cm.

7. A food emulsion product in accordance with claim 6 wherein said food emulsion product is a mayonnaise or food dressing product comprising from about 20 to about 80 weight percent of emulsified vegetable oil, from about 0.5 to about 5 weight percent of said egg yolk product (dry basis), and from about 10 to about 70 weight percent water, based on the total weight of said food emulsion product.

8. A food emulsion product in accordance with claim 6 wherein said food emulsion is a food sauce.

9. An oil-in-water type food emulsion comprising water, vegetable oil and a hydrolyzed decholesterolized egg yolk product, said hydrolyzed decholesterolized egg yolk product having a FAN in the range of from about 10,000 to about 30,000 micrograms per gram of egg protein, on a dry basis and a final interfacial tension coefficient in the range from about 3.5 to about 5.5 dynes/cm.

* * * * *

UNITED STATES PATENT AND TRADEMARK OFFICE
CERTIFICATE OF CORRECTION

PATENT NO. : 5,037,661

DATED : August 6, 1991

INVENTOR(S) : Merchant et al.

It is certified that error appears in the above-identified patent and that said Letters Patent is hereby corrected as shown below:

Column 2, lines 13-14, after "a" on line 13, insert the line on line 14, beginning with "specific".

Column 3, line 61, after "processing aid and" insert --preservative. Such egg yolk products have at least 85--.

Column 4, line 9, after "the" delete "a".

Column 8, line 14, after "109" insert --for--.

Column 10, line 48, after "MeOH" insert --)--.

Column 11, line 4, change "J. Oil" to --J. Am. Oil--.

Column 13, line 36, change "Neutrase treated" to --Neutrase-treated--.

UNITED STATES PATENT AND TRADEMARK OFFICE
CERTIFICATE OF CORRECTION

PATENT NO. : 5,037,661

DATED : August 6, 1991

INVENTOR(S) : Merchant et al.

It is certified that error appears in the above-identified patent and that said Letters Patent is hereby corrected as shown below:

Column 15, lines 20-21, claim 6, after "a" delete "in the range of from about 30,000 micrograms per gram of egg protein, on a dry basis FAN" and insert --FAN of at least about 4000 micrograms per gram of egg protein, on a dry basis--.

Column 16, line 20, claim 9, after "range" insert --of--.

Signed and Sealed this

Thirty-first Day of August, 1993

*Attest:*

BRUCE LEHMAN

*Attesting Officer*     Commissioner of Patents and Trademarks